US012643058B2

(12) United States Patent
Inoue et al.

(10) Patent No.: US 12,643,058 B2
(45) Date of Patent: Jun. 2, 2026

(54) PURIFICATION PROCESSING APPARATUS, SUBSTRATE PROCESSING SYSTEM, AND PROCESSING METHOD

(71) Applicant: Tokyo Electron Limited, Tokyo (JP)

(72) Inventors: Takeya Inoue, Yamanashi (JP); Kenji Sekiguchi, Yamanashi (JP); Mitsuaki Iwashita, Yamanashi (JP); Hirokazu Ueda, Osaka (JP); Koji Akiyama, Yamanashi (JP); Ryuichi Asako, Yamanashi (JP)

(73) Assignee: Tokyo Electron Limited, Tokyo (JP)

( * ) Notice: Subject to any disclaimer, the term of this patent is extended or adjusted under 35 U.S.C. 154(b) by 865 days.

(21) Appl. No.: 17/960,746

(22) Filed: Oct. 5, 2022

(65) Prior Publication Data

US 2023/0111710 A1     Apr. 13, 2023

(30) Foreign Application Priority Data

Oct. 7, 2021     (JP) ................................. 2021-165719

(51) Int. Cl.
  *B01D 11/04*     (2006.01)
  *B01D 17/02*     (2006.01)
  *B08B 3/08*     (2006.01)
  *C07C 29/86*     (2006.01)
(52) U.S. Cl.
  CPC ...... *B01D 11/0457* (2013.01); *B01D 11/0484* (2013.01); *B01D 11/0492* (2013.01); *B01D 17/0208* (2013.01); *B08B 3/08* (2013.01); *C07C 29/86* (2013.01)

(58) Field of Classification Search
  CPC ........... B01D 11/0457; B01D 11/0484; B01D 11/0492; B01D 17/0208; B08B 3/08; C07C 29/86
  USPC ........................................................ 134/56 R
  See application file for complete search history.

(56) References Cited

U.S. PATENT DOCUMENTS

| | | | |
|---|---|---|---|
| 2015/0013798 A1* | 1/2015 | Murayama | C07C 29/90 422/261 |
| 2017/0345683 A1* | 11/2017 | Sasaki | H01L 21/67028 |
| 2021/0199287 A1* | 7/2021 | Coil | C10L 5/44 |

FOREIGN PATENT DOCUMENTS

| | | |
|---|---|---|
| JP | 2011-012033 A | 1/2011 |
| JP | 2013-173678 A | 9/2013 |
| JP | 2016-021597 A | 2/2016 |
| JP | 2016-192435 A | 11/2016 |
| JP | 2018-517037 A | 6/2018 |
| JP | 2021-103761 A | 7/2021 |
| WO | WO 2016/189330 A1 | 12/2016 |

\* cited by examiner

*Primary Examiner* — Tinsae B Ayalew
(74) *Attorney, Agent, or Firm* — Fenwick & West LLP

(57)     ABSTRACT

A purification processing apparatus for supplying purified isopropyl alcohol to a substrate processing apparatus. The purification processing apparatus includes: a processing chamber in which unpurified isopropyl alcohol and ionic liquid are mixed, and the isopropyl alcohol and the ionic liquid are separated to purify the isopropyl alcohol; an unpurified solvent supply port configured to supply the unpurified isopropyl alcohol to the processing chamber; an ionic liquid supply port configured to supply the ionic liquid to the processing chamber; and a purified solvent outlet configured to supply the purified isopropyl alcohol from the processing chamber to the substrate processing apparatus.

10 Claims, 5 Drawing Sheets

PURIFICATION PROCESSING APPARATUS, SUBSTRATE PROCESSING SYSTEM, AND PROCESSING METHOD

CROSS-REFERENCE TO RELATED APPLICATIONS

This application claims priority to Japanese Patent Application No. 2021-165719 filed on Oct. 7, 2021, the entire contents of which are incorporated herein by reference.

TECHNICAL FIELD

The present disclosure relates to a purification processing apparatus, a substrate processing system, and a processing method.

BACKGROUND

Japanese Laid-open Patent Publication No. 2016-21597 discloses a substrate processing apparatus that cleans a wafer by supplying a chemical solution to the wafer. In this substrate processing apparatus, dilute hydrofluoric acid (DHF) liquid is discharged onto the wafer to perform chemical solution cleaning with the DHF solution. Next, pure water (rinsing liquid) is discharged onto this wafer to perform a rinsing process. Then, isopropyl alcohol (IPA) is supplied to this wafer and the wafer is dried.

SUMMARY

In one aspect, the present disclosure provides a purification processing apparatus for purifying IPA, a substrate processing system, and a processing method.

In accordance with an aspect of the present disclosure, there is provided a purification processing apparatus for supplying purified isopropyl alcohol to a substrate processing apparatus, comprising: a processing chamber in which unpurified isopropyl alcohol and ionic liquid are mixed, and the isopropyl alcohol and the ionic liquid are separated to purify the isopropyl alcohol; an unpurified solvent supply port configured to supply the unpurified isopropyl alcohol to the processing chamber; an ionic liquid supply port configured to supply the ionic liquid to the processing chamber; and a purified solvent outlet configured to supply the purified isopropyl alcohol from the processing chamber to the substrate processing apparatus.

BRIEF DESCRIPTION OF THE DRAWINGS

The objects and features of the present disclosure will become apparent from the following description of embodiments, given in conjunction with the accompanying drawings, in which.

DETAILED DESCRIPTION

Figure 1:
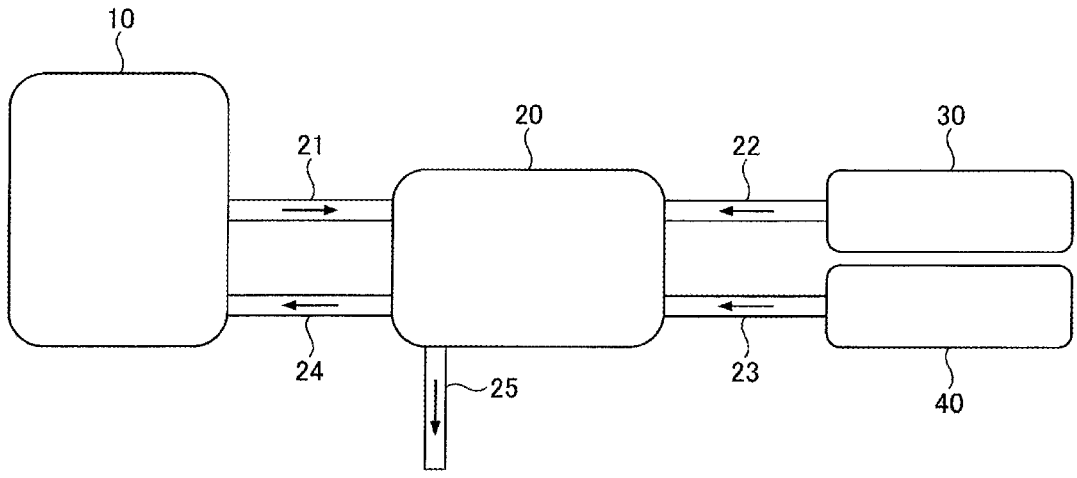
FIG. 1 is an example of a configuration diagram for illustrating a configuration of a substrate processing system according to an embodiment.

Hereinafter, embodiments of the present disclosure will be described with reference to the accompanying drawings. In each drawing, the same components are denoted by the same reference numerals, and redundant description thereof may be omitted.

FIG. 1 is an example of a configuration diagram for illustrating a configuration of a substrate processing system 1 according to an embodiment.

The substrate processing system 1 includes a substrate processing apparatus 10, a purification processing apparatus 20, an IPA supply device 30, and an ionic liquid supply device 40.

The substrate processing apparatus 10 is, e.g., a cleaning apparatus for cleaning a wafer. The substrate processing apparatus 10 includes, e.g., a spin chuck, a cleaning chemical solution supply, a rinsing liquid supply, a drying liquid supply, and an inert gas supply. The spin chuck holds the wafer and rotates. The cleaning chemical solution supply supplies a cleaning chemical solution (e.g., dilute hydrofluoric acid (DHF): dilute hydrogen fluoride aqueous solution) to the wafer held by the spin chuck. The cleaning chemical solution is not limited to and acidic cleaning chemical solution containing dilute hydrofluoric acid, and an organic solvent such as a resist remover or an acetone solvent may be used. The rinsing liquid supply supplies a rinsing liquid (e.g., pure water) to the wafer held by the spin chuck. The drying liquid supply supplies a drying liquid (isopropyl alcohol, hereinafter referred to as "IPA") to the wafer held by the spin chuck. The inert gas supply supplies an inert gas (e.g., N2 gas) to the wafer held by the spin chuck.

The substrate processing apparatus 10 cleans the wafer by performing a chemical solution treatment process, a rinsing process, and a drying process. In the chemical solution treatment process, a cleaning chemical solution (e.g., DHF solution) is supplied to the wafer while the spin chuck holds the wafer and rotates. Accordingly, a liquid film of the chemical solution is formed on a surface of the wafer, and the wafer is processed with the chemical solution. In the rinsing process, a rinsing liquid (e.g., pure water) is supplied to the wafer while the spin chuck holds the wafer and rotates. Accordingly, the chemical solution remaining on the surface of the wafer is washed away, and a liquid film of pure water is formed on the surface of the wafer. In the drying process, a drying liquid (IPA) is supplied to the wafer while the spin chuck holds the wafer and rotates. Accordingly, the rinsing liquid remaining on the surface of the wafer is washed away, and a liquid film of the drying liquid is formed on the surface of the wafer. Thereafter, the supply of the drying liquid is stopped, the wafer is rotated, and the drying liquid on the surface of the wafer is shaken off. Further, an inert gas (e.g., N2 gas) is blown onto the wafer to dry it.

The purification processing apparatus 20 purifies IPA. Specifically, IPA is purified by removing trace amounts of moisture or impurities such as metals contained in IPA. Then, the purification processing apparatus 20 supplies the purified IPA to the substrate processing apparatus 10 (drying liquid supply).

The IPA supply device 30 supplies isopropyl alcohol (IPA) to the purification processing apparatus 20.

The ionic liquid supply device 40 supplies ionic liquid to the purification processing apparatus 20. As the ionic liquid, N,N-diethyl-N-methyl-N-(2-methoxyethyl)ammonium tetrafluoroborate (hereinafter referred to as "DEME-BF4"), 1-allyl-3-ethylimidazolium tetrafluoroborate (hereinafter referred to as "AEIm-BF4"), 1-allyl-3-methylimidazolium tetrafluoroborate (hereinafter referred to as "AMIm-BF4"), 1-ethyl-3-methylimidazolium tetrafluoroborate (hereinafter referred to as "EMIm-BF4"), or the like can be used.

The substrate processing apparatus 10 and the purification processing apparatus 20 are connected by a flow path 21, and the IPA collected from the substrate processing apparatus 10 is supplied to the purification processing apparatus 20. The IPA supply device 30 and the purification processing apparatus 20 are connected by a flow path 22, and the IPA is supplied from the IPA supply device 30 to the purification processing apparatus 20. The ionic liquid supply device 40 and the purification processing apparatus 20 are connected by a flow path 23, and the ionic liquid is supplied from the ionic liquid supply device 40 to the purification processing apparatus 20. The purification processing apparatus 20 and the substrate processing apparatus 10 (drying liquid supply) are connected by a flow path 24, and the IPA purified by the purification processing apparatus 20 is supplied to the substrate processing apparatus 10 (drying liquid supply). A flow path 25 is connected to the purification processing apparatus 20 to discharge waste liquid.

Figure 2:
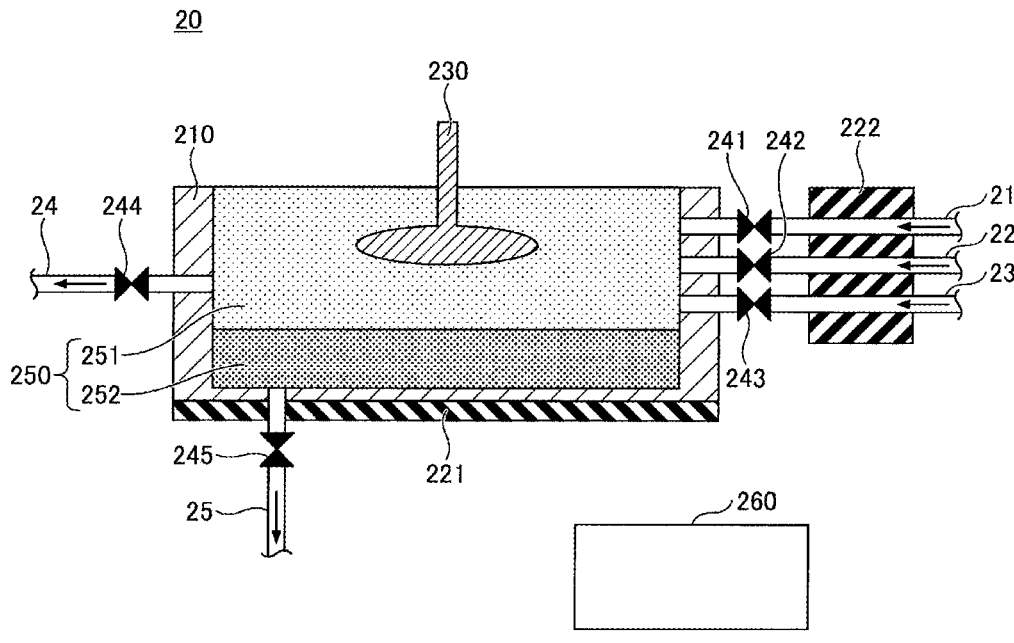
FIG. 2 is an example of a schematic cross-sectional view for illustrating a configuration of a purification processing apparatus.

Next, the purification processing apparatus 20 will be further described with reference to FIG. 2. FIG. 2 is an example of a schematic cross-sectional view for illustrating a configuration of the purification processing apparatus 20.

The purification processing apparatus 20 includes a processing chamber 210, temperature control mechanisms 221 and 222, a stirring mechanism 230, on-off valves 241 to 245, and a controller 260.

Unpurified IPA and ionic liquid are supplied to the processing chamber 210, and the IPA is purified in the processing chamber 210. The processing chamber 210 supplies the purified IPA to the substrate processing apparatus 10 (drying liquid supply).

The processing chamber 210 is connected to the flow path 21 and has an unpurified solvent inlet that supplies unpurified IPA to the processing chamber 210. Further, the processing chamber 210 is connected to the flow path 22 and has an unpurified solvent supply port that supplies the unpurified IPA to the processing chamber 210. Moreover, the processing chamber 210 is connected to the flow path 23 and has an ionic liquid supply port that supplies the ionic liquid to the processing chamber 210.

Here, the ionic liquid has insolubility in IPA. Further, the ionic liquid has a higher specific gravity than IPA. Thus, a solution 250 containing the IPA and the ionic liquid supplied to the processing chamber 210 is maintained to stand still and separated into an IPA layer 251 as an upper layer and an ionic liquid layer 252 as a lower layer as shown in FIG. 2.

Further, the processing chamber 210 is connected to the flow path 24 and has a purified solvent outlet that discharges the purified IPA from the processing chamber 210 to the substrate processing apparatus 10 (drying liquid supply). Here, the purified solvent outlet is provided at an upper side of a sidewall of the processing chamber 210 so as to collect the upper layer solution (the IPA layer 251) of the solution 250 separated into two layers in the processing chamber 210.

Further, the processing chamber 210 is connected to the flow path 25 and has a waste liquid outlet that discharges the processed ionic liquid (waste liquid) from the processing chamber 210. Here, the waste liquid outlet is provided on a bottom surface of the processing chamber 210 so as to collect the lower layer solution (the ionic liquid layer 252) of the solution 250 separated into two layers in the processing chamber 210.

The temperature control mechanism 221 controls a temperature of the solution 250 contained in the processing chamber 210. The temperature control mechanism 222 controls temperatures of the unpurified IPA and the ionic liquid supplied to the processing chamber 210 through the flow paths 21 to 23. The operations of the temperature control mechanisms 221 and 222 are controlled by the controller 260.

The stirring mechanism 230 stirs the solution 250 contained in the processing chamber 210. In other words, the stirring mechanism 230 stirs the IPA layer 251 as the upper layer and the ionic liquid layer 252 as the lower layer to mix the IPA and the ionic liquid. The operation of the stirring mechanism 230 is controlled by the controller 260.

The on-off valve 241 is provided in the flow path 21. The on-off valve 242 is provided in the flow path 22. The on-off valve 243 is provided in the flow path 23. The on-off valve 244 is provided in the flow path 24. The on-off valve 245 is provided in the flow path 25. The operations of the on-off valves 241 to 245 are controlled by the controller 260.

The controller 260 controls the overall operation of the purification processing apparatus 20 by controlling the operations of the temperature control mechanisms 221 and 222, the stirring mechanism 230, and the on-off valves 241 to 245.

Figure 3:
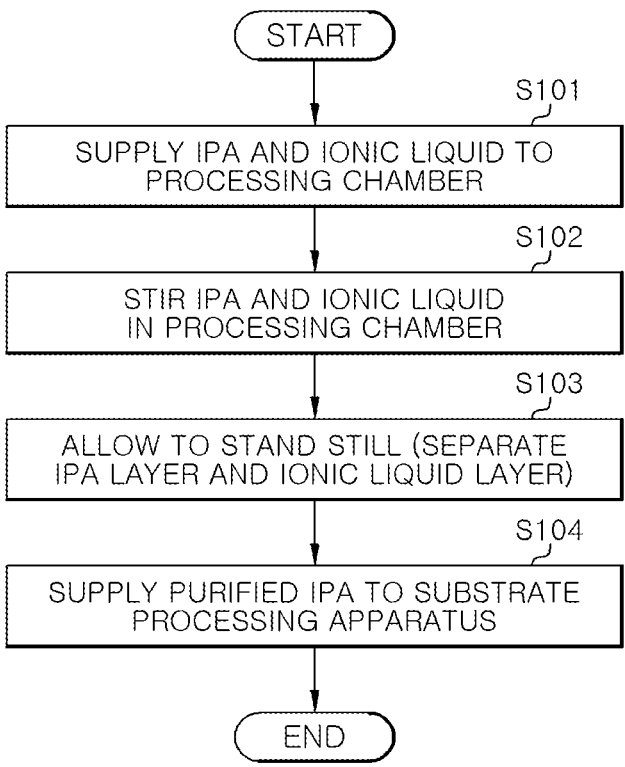
FIG. 3 is an example of a flowchart for illustrating an operation of the purification processing apparatus.

Next, a purification process of the IPA by the purification processing apparatus 20 will be described with reference to FIG. 3. FIG. 3 is an example of a flowchart for illustrating the operation of the purification processing apparatus 20.

In step S101, the controller 260 opens the on-off valve 242 and the on-off valve 243 to supply the unpurified IPA and the ionic liquid to the processing chamber 210. The controller 260 may open the on-off valve 241 and supply the IPA collected from the substrate processing apparatus 10 to the processing chamber 210. The controller 260 may also control the temperature control mechanism 222 to control the temperatures of the unpurified IPA and the ionic liquid supplied to the processing chamber 210. When the supply of the IPA and the ionic liquid to the processing chamber 210 is completed, the controller 260 closes the on-off valve 242 (241) and the on-off valve 243.

In step S102, the controller 260 operates the stirring mechanism 230 to stir the solution 250 containing the IPA and the ionic liquid in the processing chamber 210. After the stirring is completed, the controller 260 stops the operation of the stirring mechanism 230.

In step S103, the controller 260 leaves the solution 250 to stand still while the stirring mechanism 230 is stopped. This separates the IPA layer 251 and the ionic liquid layer 252.

Here, the controller 260 may control the temperature control mechanism 221 to cool (control the temperature of) the solution 250 to a temperature at which the IPA layer 251 and the ionic liquid layer 252 are separated. Further, the controller 260 may control the temperature control mechanism 221 to cool or heat (control the temperature of) the solution 250 based on the temperature of the IPA supplied to the substrate processing apparatus 10.

Accordingly, trace amounts of moisture or metals contained in the unpurified IPA move to the ionic liquid layer 252, and the moisture or the metals can be removed (purified) from the IPA of the IPA layer 251.

In step S104, the controller 260 opens the on-off valve 244 to supply the purified IPA from the IPA layer 251 to the substrate processing apparatus 10.

The ionic liquid may be re-used multiple times. Further, by opening the on-off valve 245, the IPA and the ionic liquid containing moisture or a metal can be discharged as waste liquid from the processing chamber 210.

Figure 4:
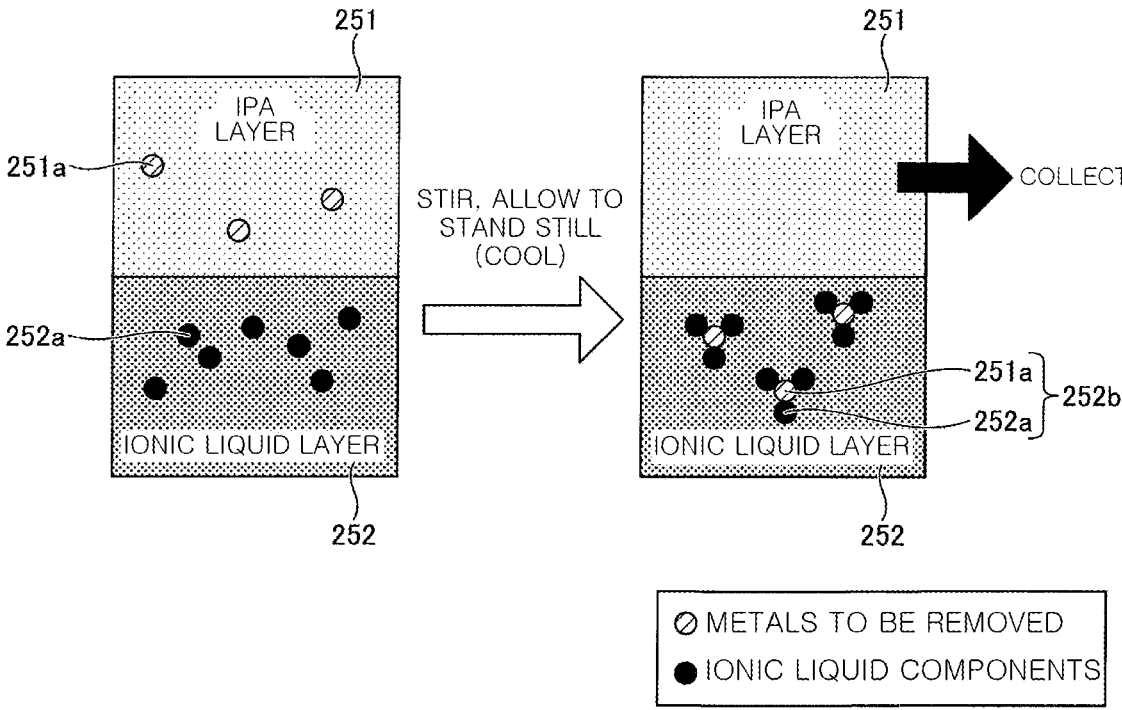
FIG. 4 is a schematic diagram for illustrating IPA purification by ionic liquid.

FIG. 4 is a schematic diagram for illustrating IPA purification by ionic liquid. Here, the case of removing trace amounts of metals contained in unpurified IPA will be described as an example.

The IPA layer 251 containing unpurified IPA contains metals to be removed 251*a*. The ionic liquid layer 252 contains ionic liquid components 252*a* such as anions and cations.

By stirring the IPA and the ionic liquid, the ionic liquid components 252*a* and the metals to be removed 251*a* come into contact with each other to form, for example, complexes 252*b*. The bonding structure between the metals to be removed 251*a* and the ionic liquid components 252*a* is not limited to a complex. By allowing the solution 250 to stand still (and cooling), the solution 250 is separated into the IPA layer 251 and the ionic liquid layer 252, and the complexes 252*b* are contained in the ionic liquid layer 252. Accordingly, the metals to be removed 251*a* can be removed from the IPA layer 251.

In FIG. 4, the case of removing metals from IPA was described as an example, but the present disclosure is not limited thereto. Trace amounts of moisture contained in unpurified IPA can be similarly removed from IPA by an ionic liquid.

Figure 5:
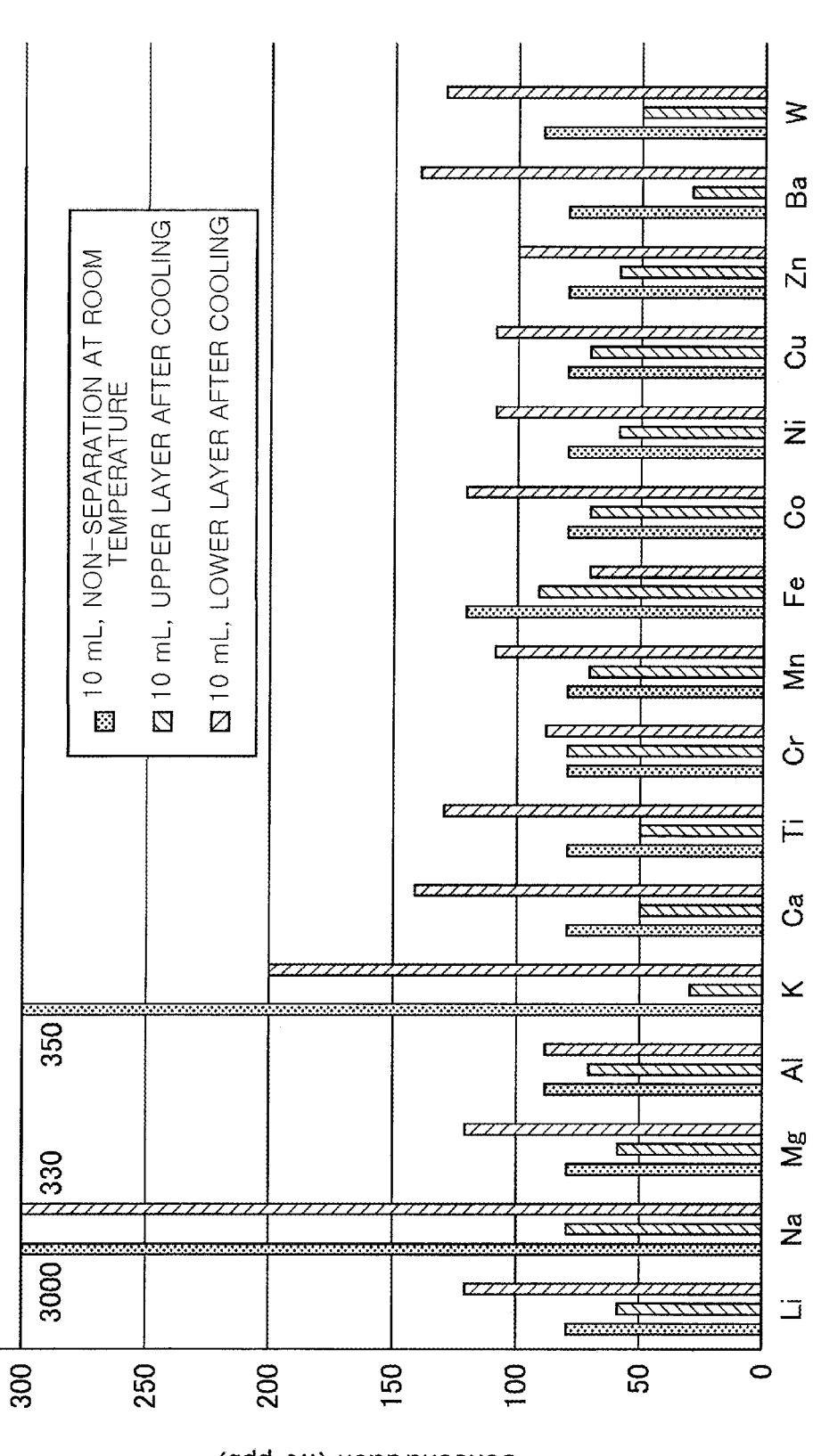
FIG. 5 is a graph showing an example of results of metal removal by ionic liquid.

FIG. 5 is a graph showing an example of results of metal removal by an ionic liquid. Here, contaminated IPA was prepared by adding a metal standard solution (a solution of 100 ppb of each metal dissolved in 5% nitric acid) to IPA. Next, 10 ml of DEME-BF4 as an ionic liquid was added to 30 ml of the contaminated IPA prepared, the mixture was stirred, cooled, and left, and the mixture was separated into the IPA as an upper layer and the ionic liquid as a lower layer. Each liquid was sampled, and mass spectrometry of each metal atom was performed by ICP-MS.

In the graph of FIG. 5, "NON-SEPARATION AT ROOM TEMPERATURE" indicates the result of the liquid after the stirring. "UPPER LAYER AFTER COOLING" indicates the result of the IPA after the separation by cooling and standing still. "LOWER LAYER AFTER COOLING" indicates the result of the ionic liquid after the separation by cooling and standing still.

As shown in FIG. 5, for metal elements other than Fe, the amount of metal detected in the lower layer was greater than that in the upper layer. In addition, for metal elements other that Cr, the amount of metal detected in the upper layer after separation is smaller than that before separation. In other words, it indicates that when the IPA and the ionic liquid are separated, the metal has moved to the lower layer, and the metal removal effect has been obtained in the upper layer.

Although FIG. 5 shows an example using DEME-BF4 as the ionic liquid, the ionic liquid is not limited thereto. By selecting a preferable ionic liquid depending on a metal to be removed from IPA, the metal to be removed can be preferably removed from IPA.

As described above, in accordance with the substrate processing system 1 of the present embodiment, the purification processing apparatus 20 can remove (purify) trace amounts of moisture and metals in IPA and supply the purified IPA to the substrate processing apparatus 10.

Here, there is known a general high-purification method in which when purifying IPA, for example, IPA is heated, and metal contaminants to be removed are chelated (complexed) using a vapor pressure difference with respect to impurities, and then removed by distillation. On the other hand, in accordance with the method for purifying IPA using the purification processing apparatus 20, IPA can be purified without being heated to a temperature for distilling IPA. Accordingly, in the substrate processing system 1 according to the present embodiment, IPA that is flammable and highly volatile can be purified without being heated to a high temperature. Further, the influence on nearby devices can be suppressed by using an ionic liquid that is flame-retardant and has no (or sufficiently low) volatility.

Further, in a configuration in which high-purity IPA is purified at a location distant from the apparatus (the substrate processing apparatus 10) using IPA and transported by tanks, pipes, or the like, the purity of IPA may deteriorate during transport. On the other hand, in the substrate processing system 1 according to the present embodiment, since the purification processing apparatus 20 can be installed at a position close to the apparatus (the substrate processing apparatus 10) using IPA, it is possible to prevent the purity of IPA from deteriorating during transport of IPA from the purification processing apparatus 20 to the substrate processing apparatus 10.

Further, the ionic liquid has high thermal stability, and can be suitably used even when the apparatus (the substrate processing apparatus 10) using IPA is in a vacuum process environment.

In FIG. 2, the case where the purification processing apparatus 20 supplies purified IPA to the substrate processing apparatus 10 has been described as an example, but the present disclosure is not limited thereto.

Figure 6:
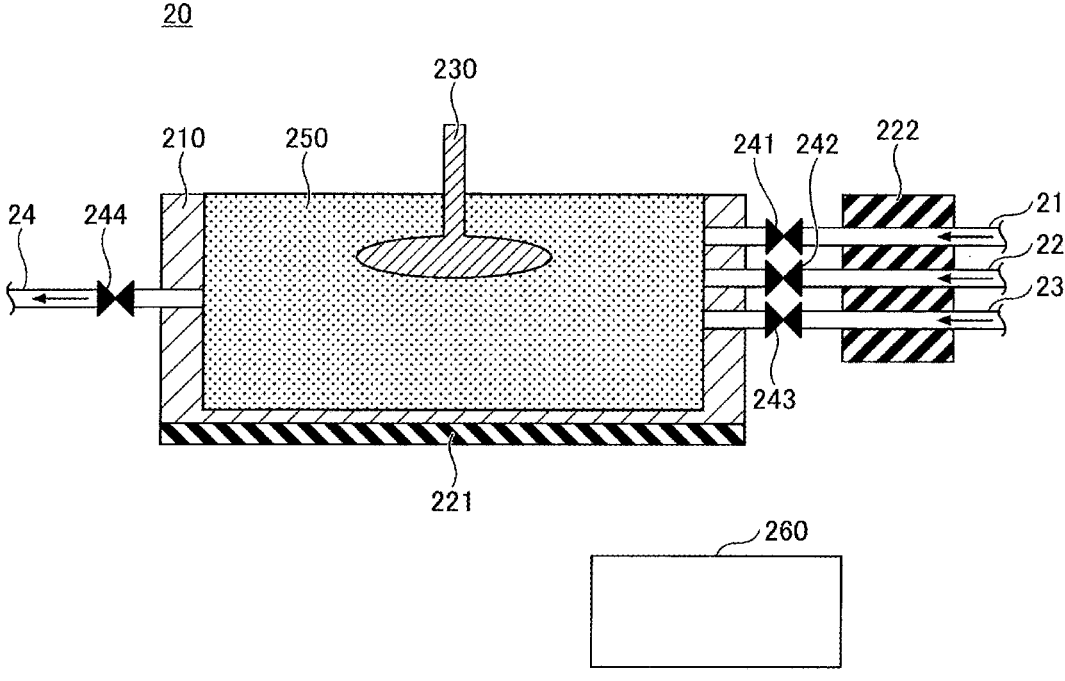
FIG. 6 is another example of the schematic cross-sectional view for illustrating the configuration of the purification processing apparatus.

FIG. 6 is another example of the schematic cross-sectional view for illustrating the configuration of the purification processing apparatus 20. As described above with reference to FIG. 4 or the like, impurities such as moisture in IPA are mixed into the ionic liquid. Further, the ionic liquid suppresses the return of the impurities mixed into ionic liquid to the IPA. In addition, the ionic liquid has high thermal stability and does not vaporize even in a vacuum process environment, for example. Therefore, even if the ionic liquid containing impurities remains in the IPA, it may not adversely affect subsequent processing. In such a case, as shown in FIG. 6, the purification processing apparatus 20 may be configured to supply the solution 250 in which the IPA and the ionic liquid are mixed to another apparatus.

The embodiments of the present disclosure should be considered illustrative and not restrictive in all respects. Also, the above-described embodiments may be omitted, substituted, or modified in various ways without departing from the scope and spirit of the appended claims.

The invention claimed is:

1. A purification processing apparatus for supplying purified isopropyl alcohol to a substrate processing apparatus including a spin chuck configured to hold and rotate a wafer, comprising:

a processing chamber in which unpurified isopropyl alcohol and ionic liquid are mixed, and the isopropyl alcohol and the ionic liquid are separated to purify the isopropyl alcohol;

an unpurified solvent supply port configured to supply the unpurified isopropyl alcohol to the processing chamber;

an ionic liquid supply port configured to supply the ionic liquid to the processing chamber;

a purified solvent outlet connected to the substrate processing apparatus and configured to supply the purified isopropyl alcohol from the processing chamber to the substrate processing apparatus; and a waste liquid outlet configured to discharge the ionic liquid from the processing chamber, wherein the purified solvent outlet connected to the substrate processing apparatus is provided at an upper side relative to the waste liquid outlet in the processing chamber.

2. The purification processing apparatus of claim 1, further comprising:

a stirring mechanism configured to stir the isopropyl alcohol and the ionic liquid in the processing chamber.

3. The purification processing apparatus of claim 1, further comprising:

a temperature control device configured to control temperatures of the isopropyl alcohol and the ionic liquid.

4. The purification processing apparatus of claim 3, wherein the temperature control device controls the temperatures of the unpurified isopropyl alcohol and the ionic liquid supplied to the processing chamber.

5. The purification processing apparatus of claim 4, wherein the temperature control device controls the temperatures of the isopropyl alcohol and the ionic liquid in the processing chamber.

6. The purification processing apparatus of claim 1, wherein the unpurified solvent supply port supplies the unpurified isopropyl alcohol from a tank containing isopropyl alcohol.

7. The purification processing apparatus of claim 1, wherein the unpurified solvent supply port supplies the isopropyl alcohol collected from the substrate processing apparatus.

8. The purification processing apparatus of claim 1, wherein the ionic liquid has a higher specific gravity than the isopropyl alcohol.

9. The purification processing apparatus of claim 1, wherein the ionic liquid is any one of DEME-BF4, AEIm-BF4, AMIm-BF4, and EMIm-BF4.

10. A substrate processing system comprising:

a substrate processing apparatus including a spin chuck configured to hold and rotate a wafer; and a purification processing apparatus for supplying purified isopropyl alcohol to the substrate processing apparatus, comprising:

a processing chamber in which unpurified isopropyl alcohol and ionic liquid are mixed, and the isopropyl alcohol and the ionic liquid are separated to purify the isopropyl alcohol, an unpurified solvent supply port configured to supply the unpurified isopropyl alcohol to the processing chamber, an ionic liquid supply port configured to supply the ionic liquid to the processing chamber, a purified solvent outlet connected to the substrate processing apparatus and configured to supply the purified isopropyl alcohol from the processing chamber to the substrate processing apparatus, and a waste liquid outlet configured to discharge the ionic liquid from the processing chamber, wherein the purified solvent outlet connected to the substrate processing apparatus is provided at an upper side relative to the waste liquid outlet in the processing chamber.

* * * * *